US012599423B2

(12) United States Patent
Vogt et al.

(10) Patent No.: US 12,599,423 B2
(45) Date of Patent: Apr. 14, 2026

(54) APPARATUS FOR PRESSING OUT BONE CEMENT, USE AND SYSTEM

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 73 days.

(21) Appl. No.: 18/921,787

(22) Filed: Oct. 21, 2024

(65) Prior Publication Data

US 2025/0134568 A1     May 1, 2025

(30) Foreign Application Priority Data

Oct. 26, 2023   (EP) ..................................... 23206000

(51) Int. Cl.
*A61B 17/88*          (2006.01)
(52) U.S. Cl.
CPC ...... *A61B 17/8822* (2013.01); *A61B 17/8833* (2013.01)
(58) Field of Classification Search
CPC ................................................. A61B 17/8822
See application file for complete search history.

(56) References Cited

U.S. PATENT DOCUMENTS

| | | | |
|---|---|---|---|
| 589,344 A | 8/1897 | Eccleston | |
| 4,312,343 A * | 1/1982 | LeVeen | A61M 5/31586 |
| | | | 604/211 |

| | | |
|---|---|---|
| 4,671,263 A | 6/1987 | Draenert |
| 4,973,168 A | 11/1990 | Chan |
| 5,100,241 A | 3/1992 | Chan |
| 5,344,232 A | 9/1994 | Nelson et al. |
| 5,586,821 A | 12/1996 | Bonitati et al. |
| 5,624,184 A | 4/1997 | Chan |
| 5,638,997 A | 6/1997 | Hawkins et al. |
| 5,997,544 A | 12/1999 | Nies et al. |
| 6,033,105 A | 3/2000 | Barker et al. |
| 6,676,663 B2 | 1/2004 | Higueras et al. |

(Continued)

FOREIGN PATENT DOCUMENTS

| | | |
|---|---|---|
| CN | 213190021 U | 5/2021 |
| CN | 218220290 U | 1/2023 |

(Continued)

OTHER PUBLICATIONS

Charnley et al., Anchorage of the femoral head prosthesis of the shaft of the femur, The Journal of Bone and Joint Surgery, vol. 42-B, No. 1, pp. 28-30 (1960), Feb. 1, 1960.

*Primary Examiner* — Andrew Yang
(74) *Attorney, Agent, or Firm* — Dicke, Billig & Czaja, PLLC

(57) ABSTRACT

An apparatus for pressing out bone cement from a cartridge, to a use of the apparatus, and to a system for pressing out bone cement. An apparatus for pressing out bone cement from a cartridge comprises a threaded rod with an external thread, a handle for rotating the threaded rod, and an adapter unit for mechanically connecting to a cartridge for bone cement. The adapter unit has a passage with an internal thread for the threaded rod. An outer surface of a thread turn of the external thread is not more than 370 mm$^2$.

15 Claims, 5 Drawing Sheets

(56)                    References Cited

U.S. PATENT DOCUMENTS

| | | | |
|---|---|---|---|
| 6,709,149 B1 | 3/2004 | Tepic | |
| 8,662,736 B2 | 3/2014 | Vogt et al. | |
| 2002/0166878 A1 | 11/2002 | Mizutani et al. | |
| 2003/0036762 A1 | 2/2003 | Kerr et al. | |
| 2003/0109884 A1* | 6/2003 | Tague ................ A61B 17/8833 |
| | | | 606/94 |
| 2012/0224452 A1 | 9/2012 | Melsheimer et al. | |
| 2016/0128752 A1 | 5/2016 | Greter et al. | |
| 2017/0340372 A1 | 11/2017 | Leonard et al. | |

FOREIGN PATENT DOCUMENTS

| | | | |
|---|---|---|---|
| DE | 3640279 | A1 | 6/1987 |
| DE | 19718648 | A1 | 11/1998 |
| DE | 102009031178 | B3 | 9/2010 |
| EP | 0692229 | A1 | 1/1996 |
| EP | 0380867 | B1 | 8/1997 |
| EP | 0796653 | A2 | 9/1997 |
| EP | 1005901 | A2 | 6/2000 |
| EP | 1016452 | A2 | 7/2000 |
| EP | 1020167 | A2 | 7/2000 |
| EP | 0796653 | B1 | 5/2004 |
| EP | 1886647 | A1 | 2/2008 |
| EP | 1741413 | B1 | 9/2009 |
| EP | 2393456 | B1 | 1/2015 |
| EP | 3054880 | B1 | 1/2020 |
| EP | 3093067 | B1 | 1/2020 |
| WO | 9416951 | A1 | 8/1994 |
| WO | 9426403 | A1 | 11/1994 |
| WO | 9967015 | A1 | 12/1999 |
| WO | 0035506 | A1 | 6/2000 |
| WO | 2012066905 | A1 | 5/2012 |
| WO | 2013141187 | A1 | 9/2013 |

* cited by examiner

APPARATUS FOR PRESSING OUT BONE CEMENT, USE AND SYSTEM

CROSS-REFERENCE TO RELATED APPLICATIONS

This application claims priority pursuant to 35 U.S.C. 119 (a) to European Patent Application No. 23206000.4, filed Oct. 26, 2023, which application is incorporated herein by reference in its entirety.

FIELD OF THE INVENTION

The invention relates to an apparatus for pressing out bone cement from a cartridge, to a use of the apparatus, and to a system for pressing out bone cement.

BACKGROUND OF THE INVENTION

Bone cement is usually produced by mixing a powder with a liquid. For example, polymethyl methacrylate (PMMA) bone cements are known which are composed of a liquid monomer component and a powder component. The monomer component generally contains the monomer methyl methacrylate and in particular an activator dissolved therein, such as N,N-dimethyl-p-toluidine. The powder component, also referred to as bone cement powder, has one or more polymers which are produced on the basis of methyl methacrylate and comonomers such as styrene, methyl acrylate or similar monomers by polymerization, preferably suspension polymerization, and in particular a radiopaque material and/or the initiator dibenzoyl peroxide. When the powder component is mixed with the monomer component, a plastically deformable paste, the actual bone cement (also termed a bone cement paste), is produced, for example by the polymers of the powder component swelling in the methyl methacrylate. When the powder component is mixed with the monomer component, the activator N,N-dimethyl-p-toluidine, for example, reacts with dibenzoyl peroxide to form radicals. The radicals formed can initiate the radical polymerization of the methyl methacrylate. As the polymerization of the methyl methacrylate progresses, the viscosity of the cement can increase until it solidifies.

PMMA bone cements are mainly used for the permanent anchoring of joint endoprostheses in the bone. In general, cement quantities of 50 g to 125 g or more are used to anchor a joint endoprosthesis. The bone cement is needed during the patient's surgery and should be provided promptly. This is the main field of application of the present invention.

Polymethylmethacrylate bone cements can be mixed in suitable mixing beakers with the aid of spatulas by mixing the cement powder with the monomer liquid. In the process, air bubbles may become incorporated into the bone cement, and can negatively influence the mechanical properties of the hardened bone cement. Other disadvantages are the need to measure the quantities manually, and adequate mixing, which is not always ensured.

Vacuum cementing systems are known for preventing air inclusions in the bone cement; of these the following are mentioned by way of example: U.S. Pat. Nos. 6,033,105, 5,624,184, 4,671,263, 4,973,168, 5,100,241, WO 99/67015 A1, EP 1 020 167 A2, U.S. Pat. No. 5,586,821, EP 1 016 452 A2, DE 36 40 279 A1, WO 94/26403 A1, EP 1 005 901 A2, EP 1 886 647 A1, U.S. Pat. No. 5,344,232. A further development in cementing technology is represented by cementing systems in which both the cement powder and the monomer liquid are already packaged in separate compartments and are mixed with one another directly before cement application in the cementing system. Such closed fully prepacked mixing systems or similar systems are described, inter alia, in the documents EP 0 380 867 B1, EP 0 796 653 B1, EP 0 692 229 A1, DE 10 2009 031 178 B3, U.S. Pat. Nos. 5,997,544, 6,709,149, WO 00/35506 A1 and EP 0 796 653 A2.

Mixing apparatuses in which an external apparatus for pressing out the bone cement is used are disclosed in WO9416951A1, EP1741413B1, EP3054880B1 and DE19718648A1. Mixing apparatuses in which a vacuum is applied to enable the transportation or mixing of a component or of the bone cement, or similar systems, are known from U.S. Pat. No. 8,662,736 and EP3093067B1. EP2393456B1 describes a mixing apparatus in which the liquid is pressed into the powder by means of an overpressure.

Manually operated discharge apparatuses, for example, are based on manually movable lever systems that drive push rods or toothed bars and are connected to the cement cartridges. By repeatedly tilting the levers, the push rod or toothed bar is moved in the direction of the discharge piston of the cartridge, wherein the discharge piston, by moving in the direction of the cartridge head, presses the polymethyl methacrylate bone cement out of the cartridge—with the discharge tubes attached in front of it. Such or similar discharge apparatuses are disclosed in U.S. Pat. No. 589, 344, U.S. Pat. No. 5,638,997 and WO9416951A.

Screw systems are commonly used to remove small amounts of cement up to approximately 10 g of bone cement, and are used to stabilize fractured vertebral bodies. These screw systems known to date have only a low mechanical load-bearing capacity and are not suitable for the discharge of larger quantities of at least 50 g of PMMA bone cement. Examples of such discharge apparatuses or similar apparatuses are the publications U.S. Pat. No. 6,676,663, US 2012/224,452, CN218220290U and CN213190021U.

The object of the invention is to enable a particularly simple manual discharge of larger quantities of bone cement. In particular, a particularly simple and cost-effective apparatus is to be created which eliminates at least some of the disadvantages of the prior art.

The object is achieved by an apparatus for pressing out bone cement. The apparatus comprises a threaded rod with an external thread, a handle for rotating the threaded rod, and an adapter unit for mechanically connecting to a cartridge for bone cement. The adapter unit has a passage with an internal thread for the threaded rod. In one embodiment, an outer surface of a thread of the external thread is at most 370 mm$^2$.

It has become apparent that the outer surface has a strong influence on friction losses when the threaded rod is rotated in the adapter unit, and thus on the force required to discharge the bone cement. The outer surface is a measure of the surface area of the external thread that contacts the internal thread. The resulting friction is accordingly proportional to the outer surface. Tests have shown that it is irrelevant whether a reduction in the outer surface is achieved by reducing the thread depth, increasing the flank angle, reducing the diameter of the threaded rod, reducing the pitch, or other measures or by combinations of different measures. Only the absolute value of the outer surface is relevant.

The bone cement is usually highly viscous. For this reason, particularly high forces are often necessary to press out the bone cement. For example, pressing out 130 g of highly viscous PMMA bone cement from a cement cartridge may require a driving force of up to 2 kN, which corresponds to a weight force of approximately 200 kg. It is thus necessary to reduce friction in order to be able to press out the bone cement with less manual force. In this way, even individuals with less strength can operate the apparatus without difficulty. This is particularly important because the bone cement after mixing continues to solidify over time and therefore the forces required for pressing increase over time. Tests have shown that with the described maximum outer surface of a thread of the external thread, it is possible for any user to easily discharge the bone cement by manually rotating the handle. With larger outer surfaces, static friction and sliding friction make discharging very difficult, and therefore result in poor ease of handling.

The apparatus can be made of plastics material, or plastics material with metal. A complicated mechanism, as in the case of a cement gun, is not necessary. No levers, bolts, pins, clamps, locking elements, toothed bars and/or gears are required. The forces required to press out the bone cement are lower than those required with conventional apparatuses, such as cement guns.

The apparatus according to the invention is easy to handle since no complicated operation of a gun is necessary. Discharge is effected simply by rotating the handle.

A thread turn means a helical line of the thread over a distance corresponding to a complete relative rotation of 360°. That is to say, one revolution is considered. The outer surface is the area of the external thread that can contact the corresponding internal thread. The outer surface of a thread turn is composed, for example, of the surface of a first (for example ascending) thread flank, of a second (for example descending) thread flank, of a surface in the region of the peak of the thread, which may, for example, extend parallel to the longitudinal axis and/or may be located between the thread flanks, and of a further surface in the region of the depression or valley of the thread, which may be located between two thread flanks. These four surfaces are added together over one revolution. In other words, the surface area between two adjacent peaks or valleys of the thread is considered. Roundings or transitions between the individual surfaces are also part of the outer surface. The respective characteristic values for the external thread of the threaded rod can apply accordingly to the internal thread of the adapter unit.

In the case of a trapezoidal thread, for example, the outer surface corresponds to the surfaces of the two thread flanks, the outward-facing surface between them in the region of the thread peak which defines the outer diameter of the external thread, and the outward-facing surface in the region of the thread valley, which defines the inner diameter of the external thread.

In the case of a multi-start thread, the surface areas of all the thread turns are added together over one revolution.

The threaded rod is designed to be rotated by manual rotation of the handle. In particular, the handle is connected to the threaded rod for conjoint rotation for this purpose. The internal thread interacts with the external thread of the threaded rod in such a way that the threaded rod can be rotated in relation to the internal thread. Internal and external threads correspond. Due to the interaction of the threaded rod with the adapter unit, the rotation of the threaded rod causes an axial translational relative movement between the threaded rod and the adapter unit. The extension direction of the threaded rod defines the axial direction of the apparatus. The threaded rod is preferably guided through the passage so that the internal thread engages with the external thread. However, the threaded rod and adapter unit can also be available separately, so that a user must first screw the threaded rod into the adapter unit before using it as intended.

The adapter unit is designed to be mechanically attached to a cartridge containing bone cement. In particular, a connection for conjoint rotation is provided at least in the direction of rotation of the threaded rod, so that rotating the threaded rod does not impair or loosen the attachment of the adapter unit to the cartridge. Typically, the adapter unit comprises one or more first fastening means and the cartridge comprises one or more second fastening means, the two fastening means being adapted to interact and thus establish the mechanical fastening. For example, the cartridge may have an external thread and the adapter unit may have a corresponding internal thread. The passage of the adapter unit is in particular centrally located.

When the adapter unit is attached to the cartridge, the axial relative movement of the threaded rod in relation to the adapter unit and thus to the cartridge causes the end of threaded rod remote from the handle to penetrate into the cartridge and thus squeeze bone cement out of the cartridge. In this way, bone cement can be pressed out of the end of the cartridge opposite the adapter unit.

In particular, the apparatus comprises, at the end of the threaded rod remote from the handle, a pressure element for exerting pressure on the bone cement in the cartridge. This pressure can be exerted directly or indirectly. For example, the pressure element can press directly on the bone cement or press on another element such as a piston of the cartridge, which in turn presses on the bone cement.

In one embodiment, the outer surface of a thread turn of the external thread is at least 230 mm$^2$.

The lower limit of the outer surface ensures that the mechanical stability of the threaded rod is maintained. If the outer surfaces are too small, for example, the thread depth or the diameter of the threaded rod will be so small that shearing of the external thread and/or torsion or buckling of the threaded rod can occur.

The pitch of the external thread also influences the force required for discharge. The pitch of the external thread is the distance measured in the axial direction that is covered in one revolution. In general, a pitch that is too short leads to a very high turn ratio and thus to increased effort during use, since a larger number of rotations must be made to discharge the bone cement. This may result in too much time being required, which is undesirable, particularly during surgery and/or when the bone cement is progressively hardening. In general, a pitch that is too long leads to a low turn ratio and therefore to a very high force for discharging the bone cement. In addition, if the pitch is too steep, the self-locking function may be reduced or eliminated, which in turn unnecessarily complicates operation. The concrete numerical values of these effects depend on different conditions such as the materials used and properties of the respective surfaces.

In one embodiment, a pitch of the external thread is at least 1 mm and/or at most 7 mm. This has proven to be particularly effective in tests. In particular, the pitch is at least 2 mm, preferably at least 3 mm, particularly preferably at least 4 mm and/or at most 5 mm, preferably at most 5 mm. In one embodiment, the pitch is approximately or exactly 4.5 mm.

In one embodiment, an outer diameter of the external thread of the threaded rod is at least 12 mm and/or at most 17 mm. The outer diameter means the maximum diameter measured between the two maximum peaks of the thread, i.e. the diameter of an imaginary circular cylinder surrounding the external thread.

In particular, the outer diameter is at least 13.5 mm and/or at most 15 mm. In one embodiment, the outer diameter is approximately or exactly 14 mm. An outer diameter of less than 12 mm is not suitable to withstand the forces or moments that occur. An outer diameter that is too large increases friction and thus the force required for discharge.

In one embodiment, the internal thread of the adapter unit contains at least 2 and/or at most 7 thread turns. This means that the stated number of revolutions is necessary to screw the threaded rod completely into the internal thread. In general, too few threads in the adapter unit leads to a low hold, low strength and/or high load on the individual thread turn. In general, too many thread turns leads to increased friction and therefore to a high force required to discharge the bone cement. The figures mentioned have proven to be particularly useful.

In particular, the internal thread contains at least 3 thread turns, preferably at least or exactly 4 thread turns and/or at most 6 thread turns, preferably at most 5 thread turns. This has proven to be the optimum of the above-mentioned effects.

In one embodiment, the thread of the threaded rod is a trapezoidal thread. This has proven to be particularly suitable.

In one embodiment, the external thread of the threaded rod has a thread depth of at least 1 mm and/or at most 4 mm. In principle, a thread depth that is too shallow leads to reduced strength and/or increased mechanical stress on the thread. In general, a thread depth that is too deep leads to increased friction and therefore to a high force required to discharge the bone cement. The figures mentioned have proven to be particularly useful.

In particular, the thread depth is not more than 2 mm and/or is approximately or exactly 1.5 mm. This has proven to be optimal with regard to the effects mentioned.

In one embodiment, for exerting pressure on the bone cement in the cartridge the apparatus has a pressure element at the end of the threaded rod which is remote from the handle. In particular, the pressure element has a flat surface.

The pressure element can be designed to exert pressure directly or indirectly as described. For example, the pressure element can be designed as a plate. In one embodiment, the pressure element is connected to the threaded rod for conjoint rotation. For example, the pressure element can be screwed onto the threaded rod, welded to it, or connected to the threaded rod by means of a plugged connection.

The pressure element can be made entirely or partially of metal or plastics material, for example of glass-fiber-reinforced plastics material and/or polyamide.

In one embodiment, the pressure element is constructed in two parts. A first part of the pressure element is connected to the threaded rod for conjoint rotation. A second part of the pressure element is connected to the first part for rotation about the longitudinal axis of the threaded rod.

The second part is used to exert pressure on the bone cement or on a part of the cartridge. The first part serves to connect the second part to the threaded rod and/or to transfer the compressive force of the threaded rod to the second part. A lubricant such as silicone may be provided between the first part of the pressure element to ensure particularly smooth relative rotation between the first part and the second part. In one embodiment, the second part surrounds the first part at least partially or circumferentially. In other words, the second part engages behind the first part. This ensures that the first part and the second part do not separate from each other. This prevents axial movement of the second part away from the first part and thus loss of the second part.

In particular, a surface of the second part facing the first part and/or a surface of the first part facing the second part is flat and/or smooth. This allows for particularly smooth relative rotation. In particular, a surface of the second part facing the first part and/or a surface facing the second part is made of metal.

In one embodiment, the adapter unit has a recess. In particular, the recess is arranged in the axial direction between a connecting element or a connecting region of the adapter unit for mechanically connecting to the cartridge of the adapter unit and/or to the internal thread or the passage. The recess is designed to at least substantially accommodate the pressure element.

In particular, the recess is circular in shape and/or arranged centrally when viewing along the longitudinal axis of the threaded rod. In particular, the recess is circular-cylindrical in shape. The recess serves to accommodate the pressure element. This means that the pressure element does not protrude beyond the recess or does not protrude significantly in the direction of the connecting element. This ensures that a connecting region of the cartridge, with which the adapter unit can be plugged onto a cartridge, for example, remains free. The recess can have an extension in the axial direction of, for example, at least 3 mm, preferably 4 mm and/or at most 10 mm, in particular at most 7 mm, preferably at most 5 mm. The axial extension of the recess may correspond approximately or exactly to the axial extension of the pressure element. The pressure element can be completely accommodated in the recess.

In one embodiment, the threaded rod comprises an inner rod, for example a metal rod, and/or a casing, for example a plastics casing.

The inner rod results in a mechanically stable threaded rod. In particular, the rod is not rotationally symmetrical. This ensures a positive connection between the material of the rod, e.g. metal, and the material of the casing, e.g., plastics material. For example, the rod can be hexagonal or square. In particular, a metal rod with or made of stainless steel such as 316L is used.

In particular, the rod is completely covered with plastics material. In particular, the thread is made of plastics material. This provides a particularly smooth thread. The rod is protected from external influences.

In one embodiment, the metal rod has a diameter of at least 7 mm and/or at most 10 mm, preferably about or exactly 8 mm. Diameters that are too small can lead to torsion and/or buckling of the threaded rod under full load. Diameters that are too large increase the diameter of the threaded rod and thus the friction.

In one embodiment, the adapter unit is designed to be connected to the cartridge by a bayonet connection. In particular, a direction of rotation of the adapter unit for connecting the adapter unit to the cartridge corresponds to a direction of rotation for screwing the threaded rod into the adapter unit.

The adapter unit therefore comprises connecting elements for creating a bayonet connection with the cartridge. The cartridge comprises in particular corresponding connecting elements. This enables a simple and secure connection. This also makes possible an interaction with existing cartridges.

The direction of rotation for screwing the threaded rod into the adapter unit is the direction in which the handle and thus the threaded rod is rotated to press the bone cement out of the cartridge. During this rotation, the connection is pushed towards the connected position. This prevents a rotation causing the connection to loosen or come loose.

In one embodiment, the threaded rod has a length of at least 15 cm and/or at most 23 cm. In one embodiment, the adapter unit has a connecting region for plugging onto a cartridge. In one embodiment, the connecting region has an inner diameter of at least 3.3 cm and/or at most 4.0 cm.

The length of the threaded rod is in particular at least 15 cm, preferably at least 17 cm, particularly preferably at least 19 cm and/or at most 25 cm, preferably at most 23 cm, particularly preferably at most 21 cm or 20 cm. This length is particularly suitable for discharging the desired amount of, for example, at least 50 g and/or at most 130 g of bone cement quickly and with reasonable effort.

The connecting region can be plugged onto one end of the cartridge. In the case of a threaded connection or a bayonet connection, this can be achieved, for example, by screwing or unscrewing. The connecting region can have an inner diameter of at least 3 cm, preferably at least 3.3 cm, in particular at least 3.5 cm and/or at most 4.0 cm, in particular at most 3.8 cm. The inner diameter of the connecting region substantially corresponds to the outer diameter of the cartridge. It has been shown that such a diameter is particularly suitable for discharging the desired amount of, for example, at least 50 g and/or at most 130 g of bone cement quickly and with reasonable effort In one embodiment, the adapter unit, the handle and/or at least part of the threaded rod is made of plastics material. In particular, the plastics material is a polyamide, polyketone, polysulfone and/or a polyoxymethylene. The plastics material is preferably polyamide 6, polyamide 6,6 and/or polyamide 12. These plastics materials have proven to be optimal in terms of strength, durability and cost.

A further aspect is the use of an apparatus according to any of the preceding claims for pressing out an amount of at least 50 g and/or at most 130 g of bone cement from a cartridge. All features, advantages and configurations of the above-mentioned apparatuses also apply to the use and vice versa.

In particular, PMMA bone cement is pressed out. In particular, this is done to anchor a joint endoprosthesis in human bone tissue. In particular, the cartridge is a cartridge of a cementing system for the anchoring of a joint endoprosthesis in human bone tissue.

A further aspect of the invention is a system for pressing out bone cement, comprising a cartridge for bone cement and an apparatus according to the invention for pressing out bone cement. In particular, the cartridge contains bone cement or at least a component for the production of bone cement. All features, advantages and embodiments of the above-mentioned apparatus and use also apply to the system and vice versa.

In particular, the cartridge comprises a connecting region which interacts with the connecting region of the apparatus such that a mechanical connection can be established between the adapter unit and the cartridge.

The cartridge can be connected at the end facing away from the adapter unit to one or more suitable hoses and/or one or more suitable tubes in order to transport the bone cement to the desired location. It is also possible to fill one or more casting molds for spacer with bone cement.

A further aspect of the invention is a method for pressing bone cement out of a cartridge, in which the handle of an apparatus according to the invention is manually rotated so that bone cement is pressed out of the cartridge. All features, advantages and embodiments of the above-mentioned apparatus, use and system also apply to the method and vice versa.

Exemplary embodiments of the invention are also explained in greater detail below with reference to figures. Features of the exemplary embodiments can be combined individually or in a plurality of the claimed subjects, unless otherwise indicated. The claimed scope of protection is not limited to the exemplary embodiments.

DETAILED DESCRIPTION OF THE INVENTION

Figure 1:
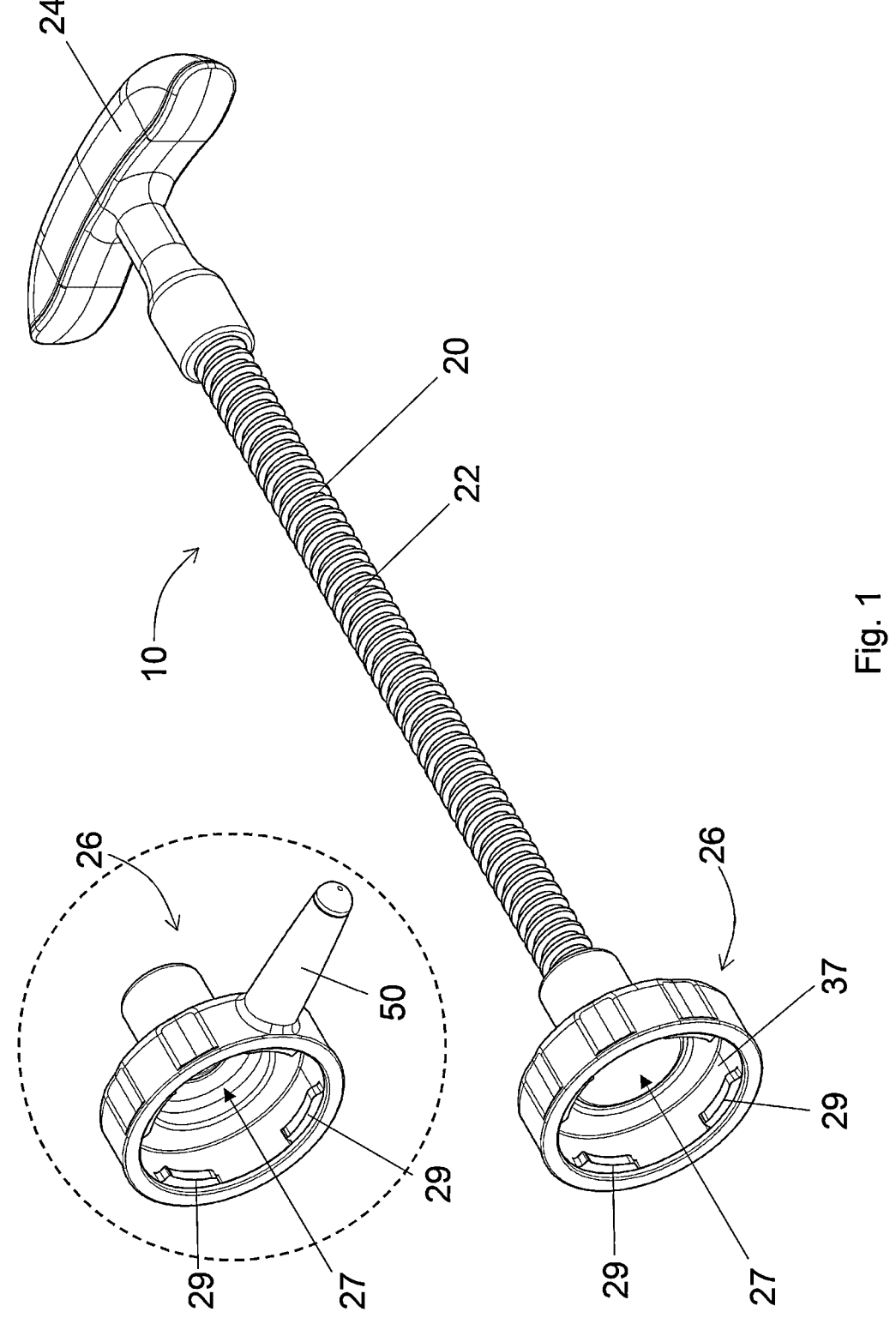
FIG. 1 is a perspective view of an apparatus according to the invention with an alternative embodiment of an adapter unit.
Figures 5, 6:
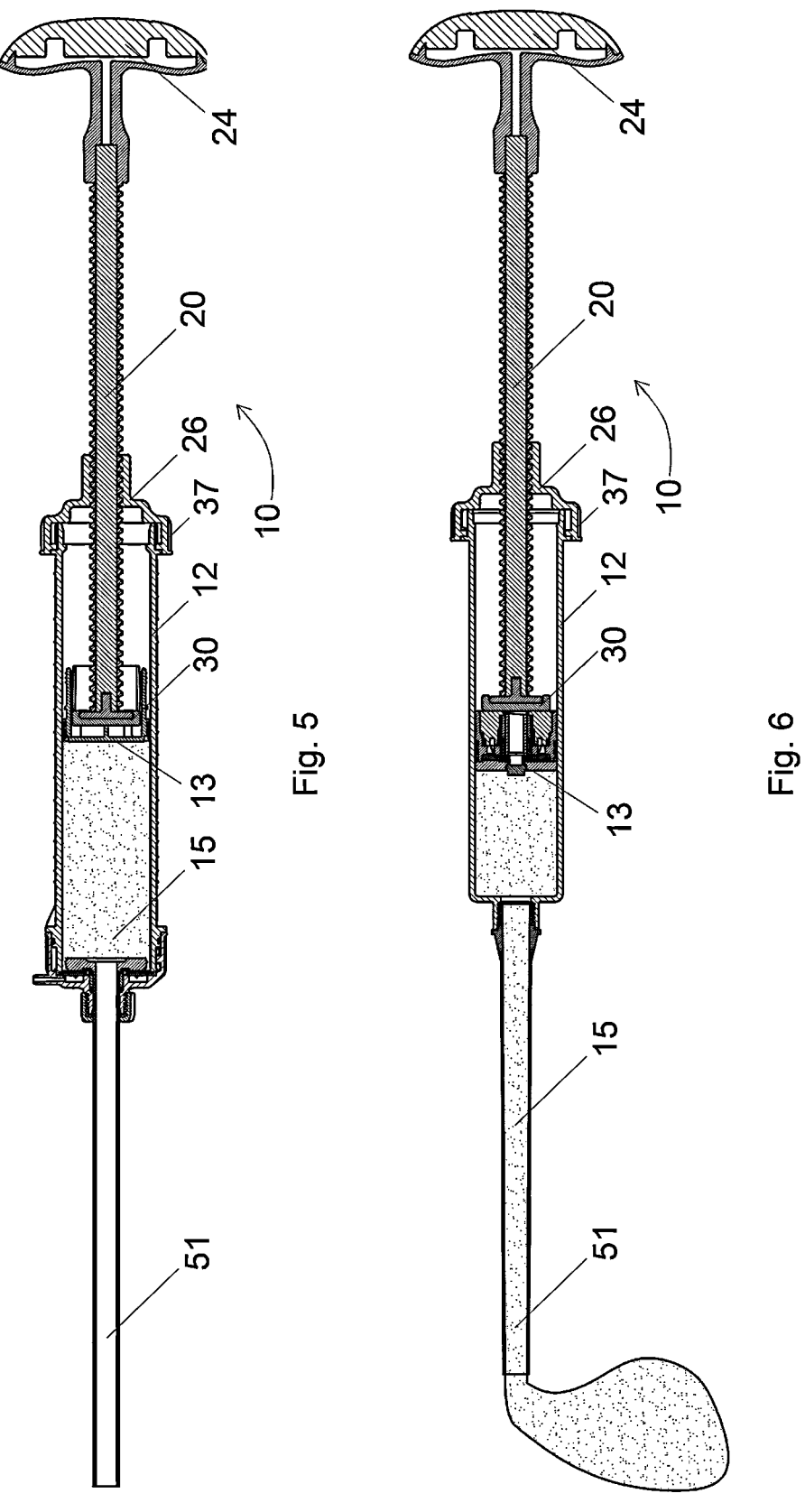
FIG. 5 is a sectional view of the use of an apparatus according to the invention.
FIG. 6 is a further sectional view of the use of an apparatus according to the invention, and, FIG. 7 is an enlarged detail of a threaded rod.

FIG. 1 is an apparatus 10 according to the invention for pressing bone cement out of a cartridge. The apparatus 10 comprises an adapter unit 26 with a connecting region 37 for mechanically connecting to a cartridge. In the embodiment shown here, the connecting region 37 can be plugged or screwed onto a corresponding region of a cartridge, as shown in FIGS. 5 and 6. In the embodiment shown here, the adapter unit 26 has connecting elements 29 for producing a bayonet connection. The direction of rotation for fastening the bayonet connection corresponds to the direction of rotation for screwing in the threaded rod 20.

The apparatus further comprises a threaded rod 20 with an external thread 22. The threaded rod 20 is passed through the passage 27 so that the external thread 22 engages with the internal thread located in the passage 27. The manually operated handle 24 for rotating is located on the end of the threaded rod 20 shown at the right. When the threaded rod 20 is rotated, the threaded rod moves axially through the adapter unit 26 so that the bone cement can be pressed out.

On the end of the threaded rod 20 remote from the handle 24, the threaded rod 20 is designed to exert a pressure or a force on the bone cement. For this purpose, a pressure element may be present, for example the pressure element 30 shown in FIG. 2.

An alternative adapter unit 26 is shown in a dashed circle. This is basically designed like the adapter unit 26 shown below it and described above, but additionally comprises a grip 50. This can have the form of a spike projecting in the radial direction. The grip 50 serves as a counterbearing during manual rotation of the handle 24. The user can use one hand to turn the handle 24 and at the same time use the other hand to fasten the adapter unit 26 or the cartridge connected to it on the grip 50. This makes possible a lower holding force and therefore easier rotation. The discharge of bone cement is further simplified.

Figure 2:
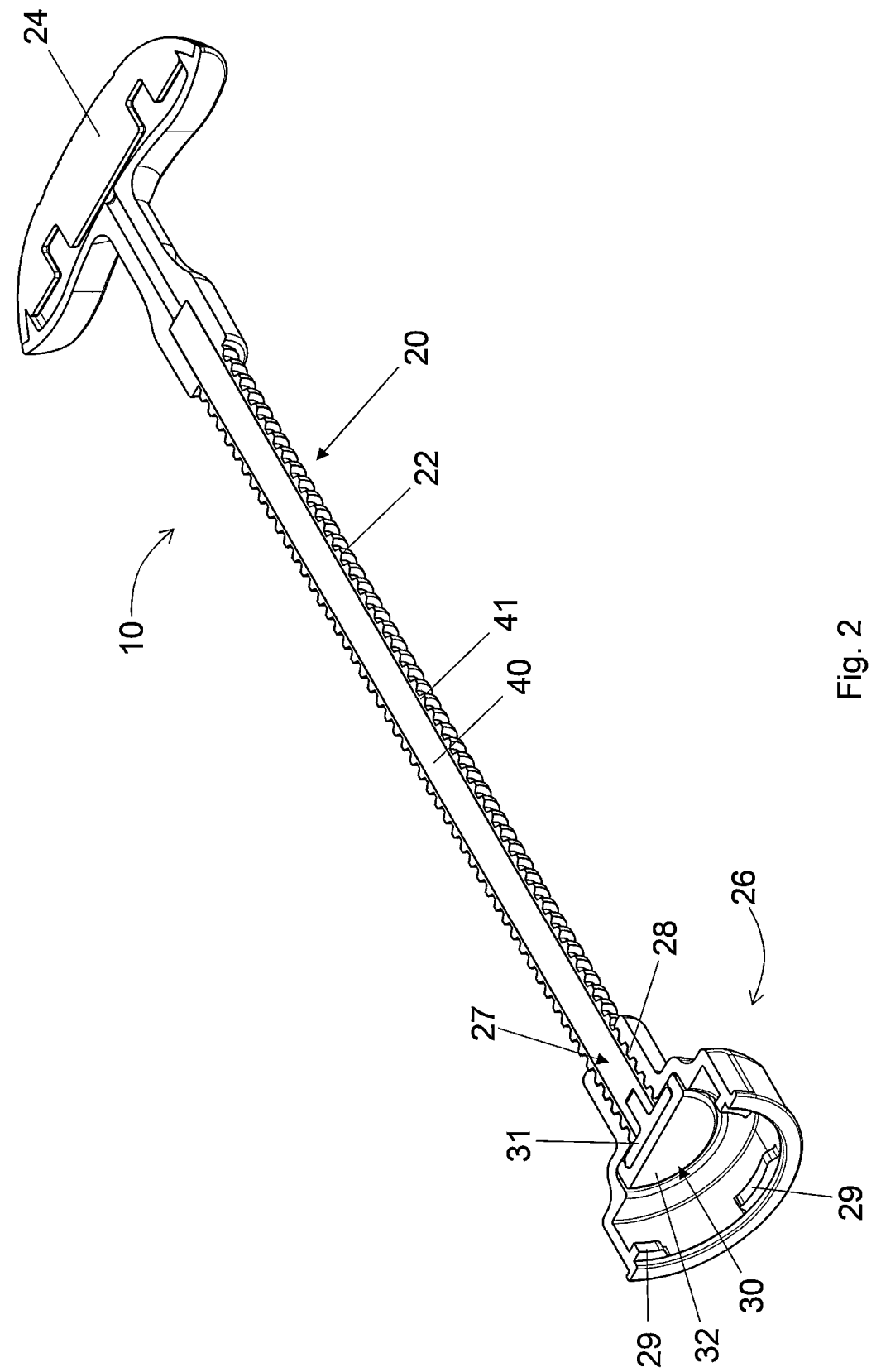
FIG. 2 is a sectional view of an apparatus according to the invention.

FIG. 2 is a similar embodiment of the apparatus 10 as FIG. 1 in a sectioned view along the central longitudinal axis of the threaded rod 20. To avoid repetition, only the differences from FIG. 1 are discussed.

It can be seen that a pressure element 30 is arranged at the end of the threaded rod 20 which is remote from the handle 24. The pressure element 30 serves to directly or indirectly exert pressure on bone cement in order to press it out of a cartridge. For example, the pressure element 30 can move a piston of the cartridge, which in turn presses the bone cement out of the cartridge.

The pressure element 30 is constructed in two parts. A first part 31 is firmly connected to the threaded rod 20, so that it rotates together with the threaded rod 20 when this rotates. A second part 32 is rotatably connected to the first part 31 so that the second part 32 does not rotate when the threaded rod 20 is rotated. In this way, no rotational movement, but only an axial pressure force, is exerted on the bone cement 15 and/or on the piston. The contacting surfaces of the first part 31 and of the second part 32 are preferably flat and smooth to enable smooth rotation.

It can also be seen that the threaded rod 20 has an inner core, in the example shown here a metal rod 40, and a casing, in the example shown here a plastics casing 41. The metal rod 40 runs centrally inside the threaded rod 20 and contributes significantly to the mechanical stability of the threaded rod 20. The plastics casing 41 forms the external thread 22 and protects the metal rod 40 from external influences. The metal rod 40 is preferably not rotationally symmetrical in order to ensure a connection to the handle 24 for conjoint rotation.

FIG. 2 also shows the internal thread 28 in the passage 27 of the adapter unit 26. The internal thread contains 4 or 5 thread turns. The external thread 22 as well as the internal thread 28 have a pitch between 3 mm and 6 mm.

Figures 3, 4:
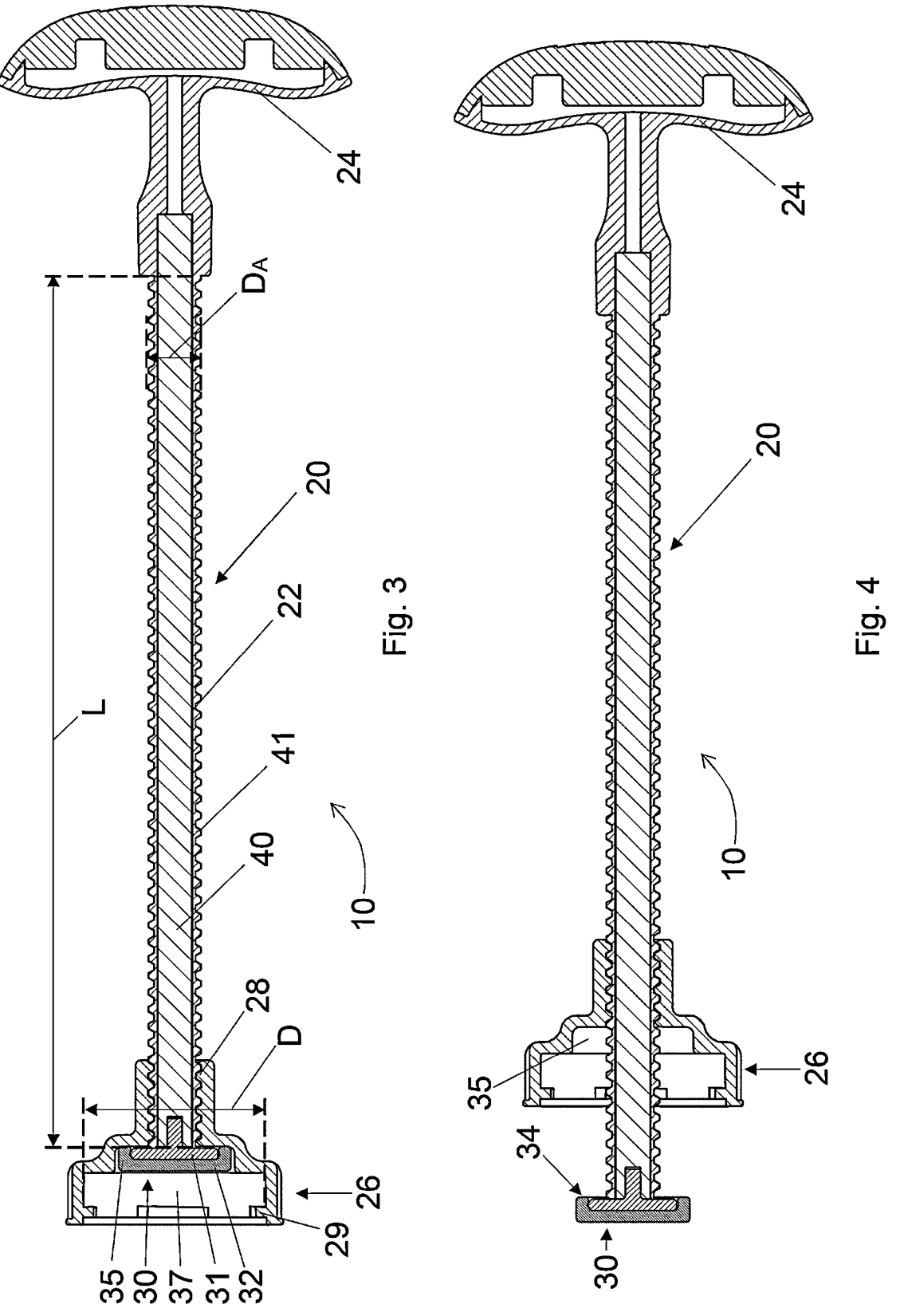
FIG. 3 is a further sectional view of an apparatus according to the invention.
FIG. 4 is a further sectional view of an apparatus according to the invention.

FIGS. 3 and 4 show similar embodiments of the apparatus 10 as FIG. 2 as a sectional drawing along the central longitudinal axis. Here, too, only the additional features are discussed, in order to avoid repetition. In FIG. 3, as in FIGS. 1 and 2, a completely unscrewed position of the threaded rod 20 from the adapter unit 26 is shown. In contrast, FIG. 4 shows a position in which the threaded rod 20 has already been partially rotated through the adapter unit 26, as occurs when pressing out bone cement.

It is shown that the adapter unit 26 has a recess 35 into which the pressure element 30 can be completely accommodated, as shown in FIG. 3. In this way, the connecting region 37 of the adapter unit 26 shown on the left side remains free of the pressure element 30. The connecting region 37 can thus be slipped over the corresponding end of the cartridge or plugged or screwed onto it without disturbing the pressure element 30.

FIG. 3 also shows some of the dimensions of the apparatus 10. The threaded rod 20 has a length L between 18 cm and 20 cm. The length L is measured between the outermost regions where the external thread 22 is present. The connecting region 37 of the adapter unit 26 has a diameter D between 34 mm and 40 mm. The diameter of the connecting region 37 corresponds approximately to the outer diameter of the corresponding connecting region of the cartridge to be connected.

It can be seen that the second part 32 of the pressure element 30 surrounds the first part 31 of the pressure element 30 and/or forms an engagement 34 with it. On the right-hand side, the in particular circumferential outer rim of the second part 32 extends inwards and engages behind the radially outer edge of the first part 31.

The first part 31 and/or the second part 32 can be designed in the form of a plate. The second part 32 may have a diameter of at least 20 mm and/or at most 30 mm, for example approximately or exactly 25 mm.

In addition, the outer diameter $D_A$ of the threaded rod 20 is shown, which is measured in the radial direction between the peaks of the external thread 22. The outer diameter $D_A$ in the example shown here is between 13.5 mm and 15 mm.

FIGS. 5 and 6 show the use of apparatuses 10 according to the invention with different cartridges 12. The connecting region 37 of the adapter unit 26 is, as described, slipped onto one end of the cartridge 12 and mechanically fastened thereto. The cartridge 12 has an outlet opening at the opposite end, to which, for example, a tube 51 for discharging the bone cement 15 is connected. Inside the cartridge is the bone cement 15. Typically, the cartridge 12 also comprises a piston 13 which is at least substantially sealed against the inner wall of the cartridge 12. The pressure element 30 of the apparatus 10 is designed, for example, to exert an axial pressure on this piston 13 in order to press the bone cement 15 out of the cartridge. FIG. 5 shows a beginning pressing process in which the pressure element 30 and the piston 13 have been pressed so far to the left that the bone cement 15 lies flat against the piston 13. FIG. 6 is a more advanced pressing process in which bone cement 15 has been conveyed through and out of the tube 51 by continued rotation of the handle 24.

Figure 7:
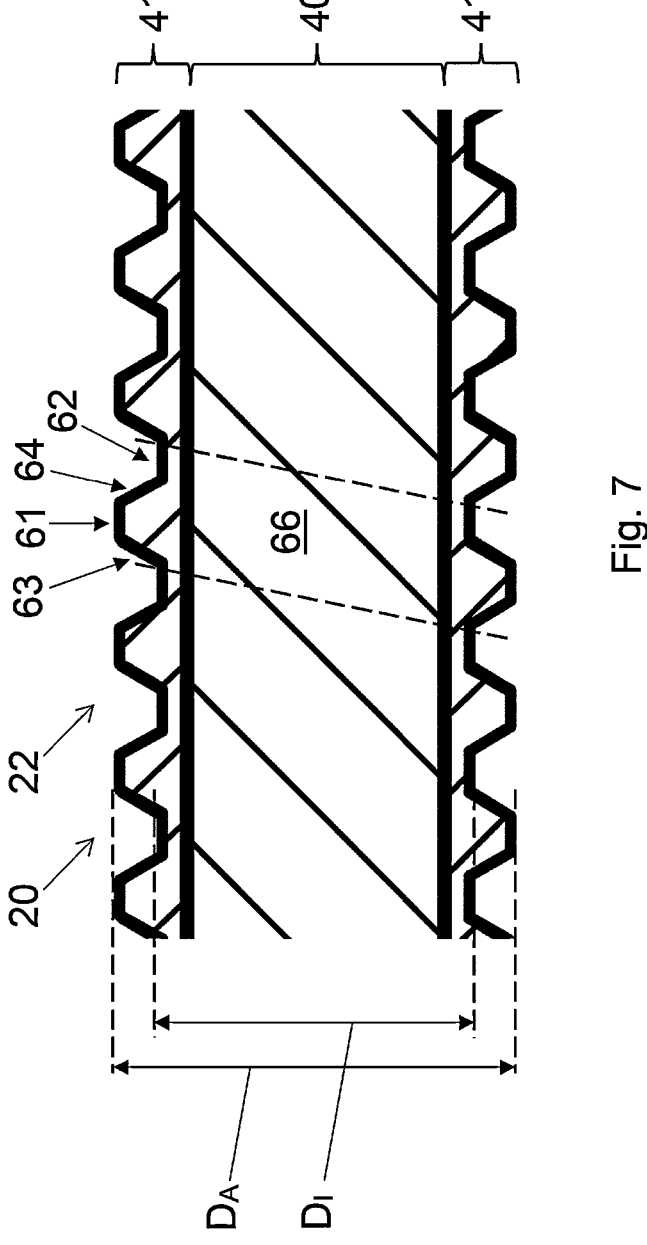

FIG. 7 is an enlarged section through a threaded rod 20. This comprises an internal metal rod 40 and a plastics casing 41 which completely encloses the metal rod 40. The outer diameter $D_A$ of the threaded rod 20 is shown, which corresponds to the maximum diameter between the peaks on both sides of the external thread 22. In addition, the inner diameter $D_I$ of the threaded rod 20 is shown, which corresponds to the minimum diameter between the depressions or valleys on both sides of the external thread 22. The thread has a thread depth between 1 mm and 2 mm. The difference between the inner diameter $D_I$ and the outer diameter $D_A$ is therefore between 2 mm and 4 mm.

A thread turn 66 is delimited by dashed lines by way of example. The thread turn corresponds to a complete rotation of the external thread 22 in relation to the corresponding internal thread. The threaded rod 20 can be designed such that an outer surface of a thread turn 66 of the external thread 22 is at most 370 mm². In the example of a trapezoidal thread shown here, the outer surface of the thread is determined as the sum of the upper surface 61, which corresponds to the surface in the region of the thread peak, the lower surface 62, which corresponds to the surface in the region of the thread depression, the first (ascending) flank surface 63 and the second (descending) flank surface 64.

In one embodiment, an outer surface of a thread turn of the external thread is at most 450 mm², in particular at most 430 mm², preferably at most 400 mm², particularly preferably at most 370 mm². In one embodiment, an outer surface of a thread turn of the external thread is at most 350 mm², in particular at most 330 mm², preferably at most 300 mm². In one embodiment, an outer surface of a thread turn of the external thread is at least 100 mm², typically at least 130 mm², in particular at least 160 mm², preferably at least 180 mm², particularly preferably at least 200 mm² and further preferably at least 215 mm². In one embodiment, an outer surface of a thread turn of the external thread is at least 250 mm², typically at least 280 mm², in particular at least 320 mm² and preferably at least 350 mm². These values may be particularly suitable depending on the design and materials.

Example 1

A apparatus was manufactured with a thread pitch of 4.5 mm, an outer diameter $D_A$ of the external thread of 14 mm and a thread depth of 1.5 mm. This has proven to be optimal for quickly pressing up to 130 g of highly viscous bone cement out of cement cartridges with little effort. A complete discharge of 130 g of bone cement from a commercially available PALAMIX® cement cartridge of the applicant could be achieved within 1.5 minutes. Similar results were achieved with the applicant's closed cementing system PALACOS PRO® (2021 version).

Example 2

Adapter units 26, threaded rods 20 with a diameter of 30 mm, 25 mm, 20 mm and 14 mm and a pitch of 4.5 mm and 7.0 mm and matching handles were manufactured from polyamide 12 using selective laser sintering (SLS). In particular, some or all components are subsequently chemically smoothed. The threaded rod 20 contains a standard stainless steel hexagonal rod inside. In particular, this was pressed into the plastics part after it had been manufactured.

For the pressing-out tests, commercially available mixing systems PALAMIX and the polymethyl methacrylate bone cement PALACOS R+G from the applicant, as well as commercially available vancomycin hydrochloride, were used.

Pressing-out tests were carried out with two packs of PALACOS R+G (2×40.8 g cement powder plus 2×18.5 g monomer liquid) mixed in a PALAMIX cartridge, resulting in approximately 118 g of bone cement. Subsequently, the bone cement was pressed out using the manufactured apparatuses, and the ease of handling of the respective apparatuses was assessed.

The results are shown in the table below.

| Outer diameter of the thread [mm] | Pitch of the thread [mm] | Outer surface of a thread turn [mm²] | Easy to press out |
|---|---|---|---|
| 30 | 7.0 | 769 | no |
| 25 | 7.0 | 632 | no |
| 20 | 7.0 | 495 | no |
| 14 | 7.0 | 331 | yes |
| 30 | 4.5 | 556 | no |
| 25 | 4.5 | 459 | no |
| 20 | 4.5 | 361 | yes |
| 14 | 4.5 | 244 | yes |

Furthermore, analogous experiments were carried out with two packs of PALACOS R+G and two monomer ampoules each containing 18.5 g of monomer liquid, to which 4.0 g of vancomycin hydrochloride was added. The theoretical amount of cement was about 126 g of cement paste. Analogous results to the first series of experiments were obtained.

| List of reference numerals | |
|---|---|
| Apparatus | 10 |
| Cartridge | 12 |
| Piston | 13 |
| Bone cement | 15 |
| Threaded rod | 20 |
| External thread | 22 |
| Handle | 24 |
| Adapter unit | 26 |
| Passage | 27 |
| Internal thread | 28 |
| Connecting element | 29 |
| Pressure element | 30 |
| First part | 31 |

-continued

| List of reference numerals | |
|---|---|
| Second part | 32 |
| Surface | 33 |
| Engagement | 34 |
| Recess | 35 |
| Connecting region | 37 |
| Metal rod | 40 |
| Plastics casing | 41 |
| Grip | 50 |
| Tube | 51 |
| Upper surface | 61 |
| Lower surface | 62 |
| First flank surface | 63 |
| Second flank surface | 64 |
| Thread turn | 66 |
| Inner diameter | D |
| Inner diameter | $D_I$ |
| Outer diameter | $D_A$ |
| Length | L |

What is claimed is:

1. An apparatus for pressing out bone cement from a cartridge, comprising a threaded rod with an external thread, a handle for rotating the threaded rod, and an adapter unit for mechanically connecting to a cartridge for bone cement, wherein the adapter unit has a passage with an internal thread for the threaded rod, wherein an outer surface of a thread turn of the external thread is at most 370 mm².

2. The apparatus according to claim 1, wherein the outer surface of a thread turn of the external thread is at least 230 mm².

3. The apparatus according to claim 1, wherein a pitch of the external thread is at least 1 mm and/or at most 7 mm.

4. The apparatus according to claim 1, wherein an outer diameter of the external thread of the threaded rod is at least 12 mm and/or at most 17 mm.

5. The apparatus according to claim 1, wherein the internal thread of the adapter unit contains at least 2 and/or at most 7 thread turns.

6. The apparatus according to claim 1, wherein the external thread of the threaded rod has a thread depth of at least 1 mm and/or at most 4 mm.

7. The apparatus according to claim 1, wherein the apparatus comprises, at the end of the threaded rod which is remote from the handle, a pressure element with a flat surface for directly or indirectly exerting pressure on the bone cement located in the cartridge.

8. The apparatus according to claim 7, wherein the pressure element is constructed in two parts, wherein a first part of the pressure element is connected to the threaded rod for conjoint rotation and a second part of the pressure element is connected to the first part for rotation about the longitudinal axis of the threaded rod.

9. The apparatus according to claim 7, wherein the adapter unit has a recess, wherein the recess is arranged in the axial direction between a connecting region or a connecting element of the adapter unit for mechanically connecting to the cartridge and the internal thread, wherein the recess is adapted to at least substantially accommodate the pressure element.

10. The apparatus according to claim 1, wherein the threaded rod comprises an inner metal rod and a plastics casing.

11. The apparatus according to claim 1, wherein the adapter unit is designed to be connected to the cartridge by a bayonet connection, wherein a direction of rotation of the adapter unit for connecting the adapter unit to the cartridge corresponds to a direction of rotation for screwing the threaded rod into the adapter unit.

12. The apparatus according to claim 1, wherein the threaded rod has a length between 15 cm and 23 cm and/or in that the adapter unit has a connecting region for plugging onto a cartridge, wherein the connecting region has an inner diameter between 3.3 cm and 4.0 cm.

13. The apparatus according to claim 1, wherein the adapter unit, the handle and/or at least part of the threaded rod is/are made of polyamide, polyketone, polysulfone and/ or polyoxymethylene.

14. A use of an apparatus according to claim 1 for pressing out an amount of between 50 g and 130 g of bone cement from a cartridge.

15. A system for pressing out bone cement, comprising a cartridge for bone cement and an apparatus according to claim 1.

\* \* \* \* \*